US00PP16582P2

(12) United States Plant Patent
Olesen

(10) Patent No.: US PP16,582 P2
(45) Date of Patent: May 30, 2006

(54) MINIATURE ROSE PLANT NAMED 'POULPAR034'

(50) Latin Name: ***Rosa* hybrid**
Varietal Denomination: Poulpar034

(75) Inventor: Mogens Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 121 days.

(21) Appl. No.: 11/002,355

(22) Filed: Dec. 1, 2004

(51) Int. Cl.
*A01H 5/00* (2006.01)

(52) U.S. Cl. ..... Plt./116

(58) Field of Classification Search ..... Plt./116, Plt./121

See application file for complete search history.

*Primary Examiner*—Anne Marie Grunberg
*Assistant Examiner*—June Hwu

(57) ABSTRACT

A new miniature rose plant that has abundant, mauve flowers and attractive foliage. The variety successfully propagates from softwood cuttings and is suitable for year-round production in commercial glasshouses. This new and distinct variety has shown to be uniform and stable in the resulting generations from asexual propagation.

1 Drawing Sheet

Botanical classification: *Rosa* hybrid.
Variety denomination: 'Poulpar034'.

SUMMARY OF THE INVENTION

The present invention constitutes a new and distinct variety of miniature rose plant which originated from a controlled crossing between the female parent, a non-patented rose named 'Korflieder', and the male pollen parent, an unnamed seedling. The two parents were crossed, and the resulting seeds were planted in a controlled environment. The new variety is named 'Poulpar034'.

The new rose may be distinguished from its seed parent by the following combination of characteristics:

1. 'Poulpar034' has larger flower buds than 'Korflieder'.
2. Flower petals of 'Korflieder' are more reflexed than those of 'Poulpar034'.

The new variety may be distinguished from its pollen parent by the following combination of characteristics:

1. 'Poulpar034' has dark shiny foliage while the parent plant has matte foliage.
2. 'Poulpar034' has a small flower diameter than the pollen parent plant.
3. 'Poulpar034' has flowers which are mauve in color while the pollen parent has pink flowers.

The objective of the hybridization of this rose variety for commercial culture was to create a new and distinct variety with unique qualities, such as:

1. Uniform and abundant mauve flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventor, and distinguish 'Poulpar034' from all other varieties of which we are aware.

As part of the rose development program, Mogens N. Olesen germinated the seeds from the aforementioned hybridization and conducted evaluations on the resulting seedlings in a controlled environment in Fredensborg, Denmark.

'Poulpar034' was selected by the inventor as a single plant from the progeny of the hybridization in June 2002.

Asexual reproduction of 'Poulpar034' by cuttings and traditional budding was first done by Mogens N. Olesen in the nursery in Fredensborg, Denmark in April 2003. This initial and other subsequent propagations conducted in controlled environments have demonstrated that the characteristics of 'Poulpar034' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'Poulpar034'. Specifically illustrated in the drawing:

FIG. 1.1; Open flower, above view. Flower buds at various stages of development;

FIG. 1.2; Flower petals, detached;

FIG. 1.3; Bare stem;

FIG. 1.4; Sepals, receptacle, and pedicel;

FIG. 1.5; Juvenile leaves;

FIG. 1.6; Mature leaves.

DETAILED DESCRIPTION OF THE VARIETY

The following is a description of 'Poulpar034', as observed in its growth in glasshouses in Burlington Ontario. Observed plants are 4 months of age and were cultivated in 10.5 cm pots. Color references are made using The Royal Horticultural Society (London, England) Colour Chart, 2001, except where common terms of color are used.

For a comparison, several physical characteristics of the rose variety 'Poulprima', a rose variety from the same inventor described and illustrated in U.S. Plant Pat. No. 9,482 and issued on Mar. 26, 1996, are compared to 'Poulpar034' in Chart 1.

CHART 1

| | 'Poulpar034' | 'Poulprima' |
|---|---|---|
| Bud color as sepals unfold | Red-Purple Group 69B with intonations of Red-Purple Group 70C. | Red-Purple Group 61C. |
| Petalage. | 55. | 30 to 35. |
| Flower bloom size. | 35 to 40 mm. | 44 to 50 mm. |

FLOWER AND FLOWER BUD

Blooming habit: Continuous.

Flower bud:

*Size.*—Upon opening, 20 mm in length from base of receptacle to end of bud. 10 mm in diameter.

*Bud form.*—Urceolate.

*Bud color.*—As sepals unfold, Red-Purple Group 69B with intonations of Red-Purple Group 70C.

*Sepals.*—Upper Surface: Color: Green Group 138B. Texture: Moderate pubescence. Lower Surface: Color: Yellow-Green Group 144A. Texture: Smooth with few stipitate glands. Shape: Apex: Cirrhose. Base: Flat at union with receptacle. Margins: Margins have weak foliaceous appendages on three of the five sepals. Two of the five sepals have margins which are entire. Size: 21 mm long by 9 mm wide.

*Receptacle.*—Surface Texture: Smooth. Shape: Funnel shaped. Size: 7 mm (h)×7 mm (w). Color: Yellow-Green Group 144A.

*Peduncle.*—Surface: Somewhat rough with stipitate glands. Length: 20 to 25 mm. Diameter: 2.5 mm average. Color: Yellow-Green Group 144A. Strength: Medium.

*Borne.*—Singularly.

Flower bloom:

*Fragrance.*—None.

*Duration.*—As a pot plant, flowers last from 21 to 28 days. Petals fall cleanly away from plant after flowers have fully matured.

*Size of open flower.*—Diameter is 35 to 40 mm. Depth is 15 to 18 mm.

*Form.*—Fully opened flowers form a very double rosette, with many slightly overlapping petals of different sizes.

*Shape of flower when viewed from the side.*—Upon opening, upper part: Flat. Upon opening, lower part: Flat. Open flower, upper part: Flattened convex. Open flower, lower part: Slightly concave.

Petalage: Normally 55 petals, 15 to 20 of which are petaloids.

Flower color:

*Upon opening, petals.*—Outermost petals: Upper Surface: Purple Group 75B to Red-Purple Group 70D with underlying intonations of Red-Purple Group 69C. Basal zone margins exhibit darker intonations of Red-Purple Group 70C. Lower Surface: Purple Group 75B to Red-Purple Group 70D with underlying intonations of Red-Purple Group 69C at margins. Basal zone margins exhibit intonations of Red-Purple Group 70C. Innermost petals: Upper Surface: Purple Group 75B to Red-Purple Group 70D with underlying intonations of Red-Purple Group 69C. Basal zone margins exhibit darker intonations of Red-Purple Group 70C. Lower Surface: Purple Group 75B to Red-Purple Group 70D with underlying intonations of Red-Purple Group 69C at margins. Basal zone margins exhibit darker intonations of Red-Purple Group 70C.

*Upon opening, basal petal spots.*—Upper Surface: Green-Yellow Group 1C. Lower Surface: Green-Yellow Group 1D.

*After opening, petals.*—Outermost petals: Upper surface: Purple Group 75B to Red-Purple Group 70D with underlying intonations of Red-Purple Group 69C. Basal zone margins exhibit darker intonations of Red-Purple Group 70C. Lower Surface: Purple Group 75B to Red-Purple Group 70D with underlying intonations of Red-Purple Group 69C at margins. Basal zone margins exhibit darker intonations of Red-Purple Group 70C. Innermost petals: Upper Surface: Purple Group 75B to Red-Purple Group 70D with underlying intonations of Red-Purple Group 69C. Basal zone margins exhibit darker intonations of Red-Purple Group 70C. Lower Surface: Purple Group 75B to Red-Purple Group 70D with underlying intonations of Red-Purple Group 69C at margins. Basal zone margins exhibit darker intonations of Red-Purple Group 70C.

*After opening, basal petal spots.*—Upper Surface: Green-Yellow Group 1C. Lower Surface: Green-Yellow Group 1D.

General tonality: On open flower Purple Group 75B. No change in the general tonality of the end of the 15$^{th}$ day. Afterwards, general tonality is Purple Group 75D.

Petals:

*Petal reflex.*—Somewhat reflexed.

*Petal margin.*—Entire and uniform.

*Shape.*—Generally broad elliptical. Base: Variable from acute to obtuse. Apex: Rounded. Occasionally mucronate.

*Size.*—On average, 19 mm (l)×18 mm (w).

*Thickness.*—Average.

*Arrangement.*—Not formal.

*Texture.*—Smooth.

Petaloids:

*Quantity.*—Normally 15 to 20.

*Size.*—7 mm (l)×5 mm (w).

*Shape.*—Irregular. Base: Acute. Apex: Round to acute.

*Petaloid color.*—Upper surface: Purple Group 75B to Red-Purple Group 70D with underlying intonations of Red-Purple Group 69C. Lower Surface: Purple Group 75B to Red-Purple Group 70D with underlying intonations of Red-Purple Group 69C at margins.

*Basal petal spots.*—Upper surface: Yellow Group 9B. Lower surface: Yellow Group 9C.

Reproductive organs;

*Pollen.*—None observed.

*Anthers.*—Size: 2 mm long. Color: Yellow Group 10A. Quantity: 25 to 30.

*Filaments.*—Color: Yellow Group 9C. Length: 2 to 3 mm.

*Pistils.*—Length: 5 to 6 mm. Quantity: 20 to 25.

*Stigmas.*—Superior relative to the length of the filaments and the height of the anthers. Color: White Group 155A.

*Styles.*—Color: White Group 155A.

*Seed formation.*—None observed.

PLANT

Plant growth: Vigorous, compact, upright to bushy. When grown as a 8–11 cm pot plant on its own roots, the average height of the plant itself is 25 to 30 cm and the average width is 15 to 20 cm.

Stems:

*Color.*—Juvenile and mature stems are Yellow-Green Group 144A.

*Internodal distance.*—20 mm.

*Diameter.*—Average is 2.75 mm.

*Length of stems.*—15 to 20 cm from base of the plant to the flowering portion.

*Surface texture.*—Young wood: Smooth. Older wood: Smooth.

Thorns:

*Incidence.*—10 thorns per 10 cm of stem observed.

*Average length.*—4 mm.

*Color.*—Juvenile and mature thorns are Greyed-Orange Group 163D.

*Shape.*—Flat.

Plant foliage: 5 Leaflets on normal leaves in middle of the stem.

*Compound leaf size.*—75 mm (l)×50 mm.

*Quantity.*—5 leaves per 10 cm of stem.

*Color of juvenile foliage.*—Upper Leaf Surface: Yellow-Green Group 146A with marginal anthocyanic intonations Greyed-Red Group 179A. Lower Leaf Surface: Green Group 138B. Anthocyanic intonations generalized throughout the leaflet are Greyed-Orange 176A in color.

*Color of mature foliage.*—Upper Leaf Surface: Yellow-Green Group 146A to 147A. Lower Leaf Surface: Green Group 138B.

Plant leaves and leaflets:

*Stipules.*—Size: 6 mm in length. Shape: Linear, slightly broad based with outward extending apecies. Margins: Finely serrated with few stipitate glands. Color: Yellow-Green Group 146B.

*Petiole.*—Length: 15 mm to 18 mm. Diameter: 1 mm. Color: Upper surface: Yellow-Green Group 146B and, on occasion, Greyed-Orange Group 166A. Lower surface: Yellow-Green Group 146C. Observations: No stipitate glands observed. Lightly pubescent. Few small prickles observed.

*Rachis.*—Size: 20 mm. Color: Upper surface: Yellow-Green Group 146B and, on occasion, Greyed-Orange Group 166A. Lower surface: Yellow-Green Group 146C. Underneath: Lightly pubescent. Few stipitate glands observed. Few small prickles observed.

*Leaflet.*—Size: 37 mm in (l)×23 mm (w). Margin: Serrated. General Shape: Elliptical. Apex Shape: Acuminate. Base Shape: Obtuse. Texture: Smooth. Thickness: Average. Arrangement: Odd pinnate. Venation: Reticulate. Leaf Gloss: Somewhat glossy.

Disease resistance: Average resistance to powdery and downy mildews, black spot, and *Botrytis* under normal growing conditions in Burlington, Canada.

It is claimed:

1. A new and distinct variety of rose plant of the miniature class named 'Poulpar034', substantially as illustrated and described herein, due to its abundant, mauve flowers, vigorous growth, compact habit, suitability for production from softwood cuttings in pots, and durable flowers and foliage that make the variety suitable for distribution in the floral industry.

* * * * *

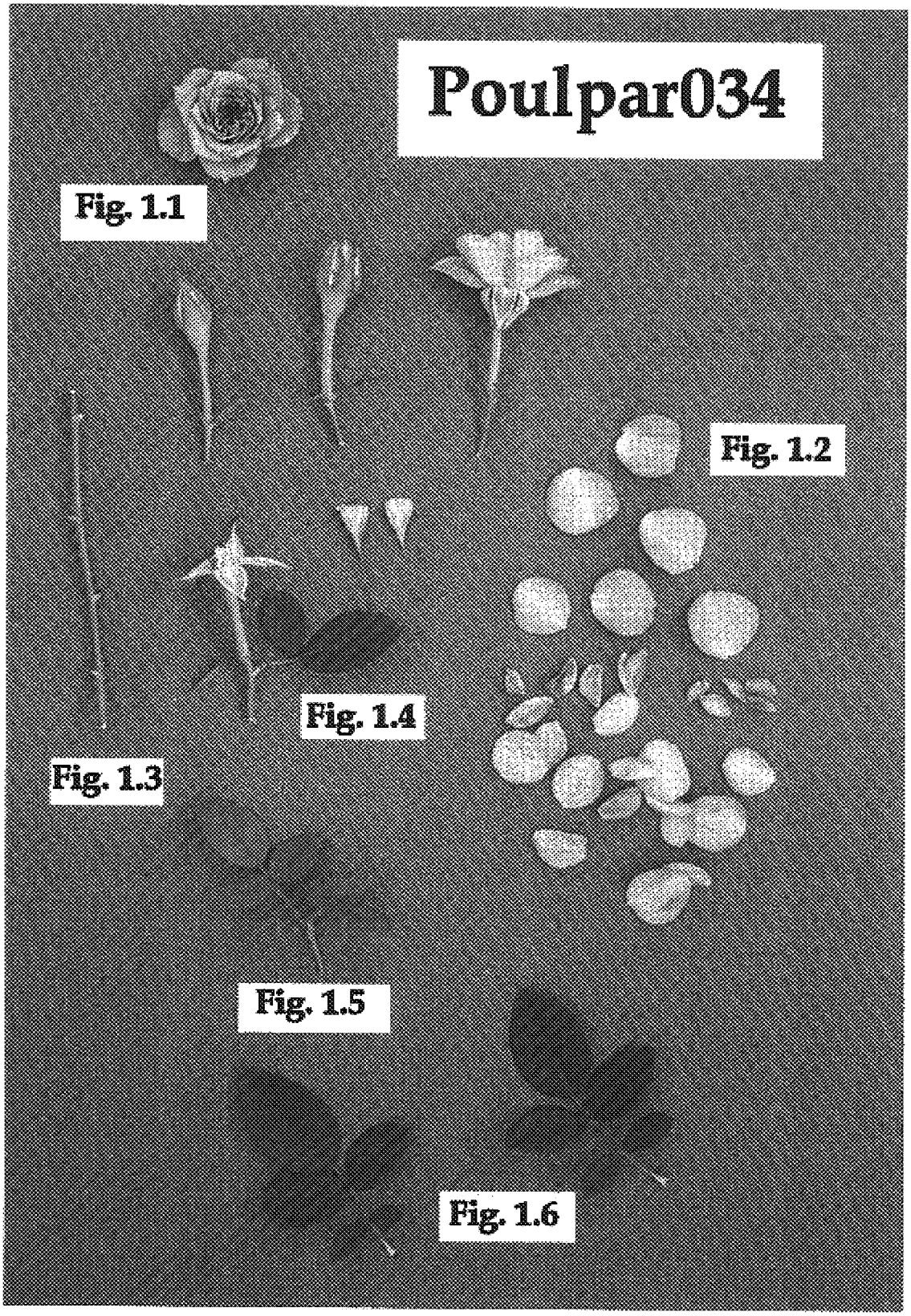
Poulpar034
Fig. 1.1
Fig. 1.2
Fig. 1.4
Fig. 1.3
Fig. 1.5
Fig. 1.6